(12) United States Patent
Riobo Aboy et al.

(10) Patent No.: US 8,298,151 B2
(45) Date of Patent: Oct. 30, 2012

(54) METHOD AND APPARATUS FOR EVALUATION OF FLUID RESPONSIVENESS

(75) Inventors: Pedro Mateo Riobo Aboy, Beaverton, OR (US); Roberto Hornero Sánchez, Valladolid (ES); Carlos Gómez Peña, Valladolid (ES)

(73) Assignee: Universidad De Valladolid, Valladolid (ES)

( * ) Notice: Subject to any disclaimer, the term of this patent is extended or adjusted under 35 U.S.C. 154(b) by 754 days.

(21) Appl. No.: 12/363,786

(22) Filed: Feb. 1, 2009

(65) Prior Publication Data

US 2009/0198140 A1    Aug. 6, 2009

Related U.S. Application Data

(60) Provisional application No. 61/025,309, filed on Feb. 1, 2008.

(51) Int. Cl.
*A61B 5/02* (2006.01)
*A61B 5/029* (2006.01)
(52) U.S. Cl. .................. 600/485; 600/508; 600/509
(58) Field of Classification Search .................. None
See application file for complete search history.

(56) References Cited

U.S. PATENT DOCUMENTS 6,776,764 B2    8/2004    Pinsky
7,225,013 B2    5/2007    Geva et al.
7,422,562 B2    9/2008    Hatib

OTHER PUBLICATIONS

Huang et al. Novel method of fast automated discrimination of sleep stages. Proceedings of the 25th Annual International Conference of the IEEE EMBS, Cancun, Maxico, Sep. 17-21, 2003, pp. 2273-2276.*
Chen et al. Complexity-measure-based sequential hypothesis testing for real-time detection of lethal cardiac arrhythmiacs. EURASIP Journal on Advances in Signal Processing, 2007, pp. 1-8.*
Xu et al. Arrhythmic pulses detection using Lempel-Ziv complexity analysis. EURASIP Journal on Applied Signal Processing, 2006, pp. 1-12.*
Hornero R, et al. Complexity Analysis of Arterial Pressure During Periods of Abrupt Hemodynamic Changes. IEEE Transactions on Biomedical Engineering, vol. 55, No. 2, Feb. 2008.

* cited by examiner

*Primary Examiner* — Shafiqul Haq
(74) *Attorney, Agent, or Firm* — Mateo Aboy; Aboy & Associates PC

(57) ABSTRACT

The present invention discloses a method and related apparatus for determining a cardiac parameter from either the arterial blood pressure signal or the photoplethysmographic signal to quantify the degree of amplitude modulation due to respiration (pulse pressure variation) and predict fluid responsiveness. The method involves the application of Lempel-Ziv complexity to a filtered and segmented physiologic signal for direct determination of the fluid status of a patient. Real-time monitoring of fluid status involves the implementation of the disclosed method as part of a bedside monitoring apparatus.

4 Claims, 2 Drawing Sheets

METHOD AND APPARATUS FOR EVALUATION OF FLUID RESPONSIVENESS

CROSS REFERENCE TO RELATED APPLICATIONS

This application claims the benefit of PPA No. 61/025,309 filed on 2008-02-01 by the present inventors, which is incorporated by reference.

BACKGROUND

1. Field of Invention

This invention relates in general to cardiac monitoring and in particular to dynamic estimation of fluid responsiveness.

2. Related Art

Indicators and methods for noninvasive determination of fluid status of patients are important for real-time monitoring of the condition of critical care patients.

Numerous studies have demonstrated that pulse pressure variation (PPV) is one of the most sensitive and specific predictors of fluid responsiveness. Specifically, PPV has been shown to be useful as a dynamic indicator to guide fluid therapy in different patient populations receiving mechanical ventilation. For instance, PPV was found to exhibit better performance as a predictor of fluid responsiveness in patients before off-pump coronary artery bypass grafting than standard static preload indexes. PPV has also been shown to be useful for predicting and assessing the hemo-dynamic effects of volume expansion and a reliable predictor of fluid responsiveness in mechanically ventilated patients with acute circulatory failure related to sepsis. Another study concluded that PPV can be used to predict whether or not volume expansion will increase cardiac output in postoperative patients who have undergone coronary artery bypass grafting. A critical review of studies investigating predictive factors of fluid responsiveness in intensive care unit patients concluded that PPV and other dynamic parameters should be used preferentially to static parameters to predict fluid responsiveness.

The standard method for calculating PPV often requires simultaneous recording of arterial and airway pressure. Pulse pressure (PP) is calculated on a beat to beat basis as the difference between systolic and diastolic arterial pressure. Maximal PP ($PP_{max}$) and minimal PP ($PP_{min}$) are calculated over a single respiratory cycle, which is determined from the airway pressure signal. Pulse pressure variations $\Delta PP$ are calculated in terms of $PP_{max}$ and $PP_{min}$ and expressed as a percentage, $$PPV(\%) = 100 \times \frac{PP_{max} - PP_{min}}{(PP_{max} + PP_{min})/2} \quad (1)$$

Despite the usefulness of PPV, automatic determination of PPV is a difficult problem and it is often very difficult to accurately determine this parameter automatically in regions of abrupt hemodynamic changes such as operating room conditions or regions with artifact. Respiratory variations in arterial pulse pressure calculated manually (PPVman) are accurate predictors of fluid responsiveness in mechanically ventilated patients. However, they cannot be continuously monitored. Thus, it is not possible o to conveniently monitor this manual index in the operating room or in the intensive care unit. Commercially available systems capable of monitoring PPV do not work well in regions of abrupt hemodynamic changes.

As a consequence, other simpler methods for prediction of fluid responsiveness have been proposed. These methods have the advantage that can be obtained by direct application of a simple formula to the arterial blood pressure signal. For example, U.S. Pat. No. 7,422,562 discloses a method for determining a cardiac parameter equal to or derivable from cardiac stroke volume variation (SVV) comprising: inputting a waveform data set corresponding to arterial blood pressure over a computation interval that covers at least two cardiac cycles; calculating a standard deviation value for the waveform data set over each cardiac cycle; and calculating an estimate of the SVV as a function of the standard deviation values.

The ideal method should be a predictive of fluid responsiveness as PPV but significantly easier to calculate and provide accurate information about fluid status in operating room conditions.

BRIEF SUMMARY OF THE INVENTION

The present invention discloses a method and related apparatus for determining a cardiac parameter from either the arterial blood pressure signal or the photoplethysmographic signal to quantify the degree of amplitude modulation due to respiration (pulse pressure variation) and predict fluid responsiveness. The method involves the application of Lempel-Ziv complexity to a filtered and segmented physiologic signal for direct determination of the fluid status of a patient. Real-time monitoring of fluid status involves the implementation of the disclosed method as part of a bedside monitoring apparatus.

DETAILED DESCRIPTION

The present invention discloses a method and related apparatus for determining a cardiac parameter from either the arterial blood pressure signal or the photoplethysmographic signal to quantify the degree of amplitude modulation due to respiration (pulse pressure variation) and predict fluid responsiveness. The method involves the application of Lempel-Ziv complexity to a filtered and segmented physiologic signal for direct determination of the fluid status of a patient. Real-time monitoring of fluid status involves the implementation of the disclosed method as part of a bedside monitoring apparatus. The method is comprised of the following steps:

Lowpass the input physiologic signal to remove frequencies outside the region of physiologic interest, $$x^l(n) = x(n) * h_l(n)$$

where * denotes the operation of convolution, $h_l(n)$ denotes the impulse response of a lowpass filter with cutoff frequency $f_c^l$. According to one embodiment of the present invention the cutoff frequency of the lowpass filter is 12 Hz ($f_c^l = 12$ Hz).

Highpass the resulting signal $x_l(n)$ to eliminate the local trend, $$x^h(n) = x_l(n) * h_h(n)$$

where * denotes the operation of convolution, $h_h(n)$ denotes the impulse response of a highpass filter with cutoff frequency $f_c^h$. According to one embodiment of the present invention the cutoff frequency of the highpass filter is 0.1 Hz ($f_c^l$=0.1 Hz).

Segment the resulting signal $x_h(n)$ into N locally stationary segments, $$[x_1^h(n), x_2^h(n), \ldots, x_N^h(n)]$$

Calculate the Lempel-Ziv complexity of each segment $\{x_k^h(n)\}_{k=1}^N$ $$y(n)=LZ\{[x_1^h(n), x_2^h(n), \ldots, x_N^h(n)]\}$$

Monitor the resulting Lempel-Ziv complexity values, y(n), to determine fluid status and predict fluid responsiveness by means of comparing y(n) against a threshold $t_r$. According to one embodiment of the present invention $t_r$ 32 0.23, $$r=I\{y(n)>t_r\} \qquad (1)$$

where I denotes an indicator function which equals to 1 when $y(n)>t_r$ and 0 otherwise. Consequently, when r is equal to one the patient is responsive to fluid therapy.

Figure 1:
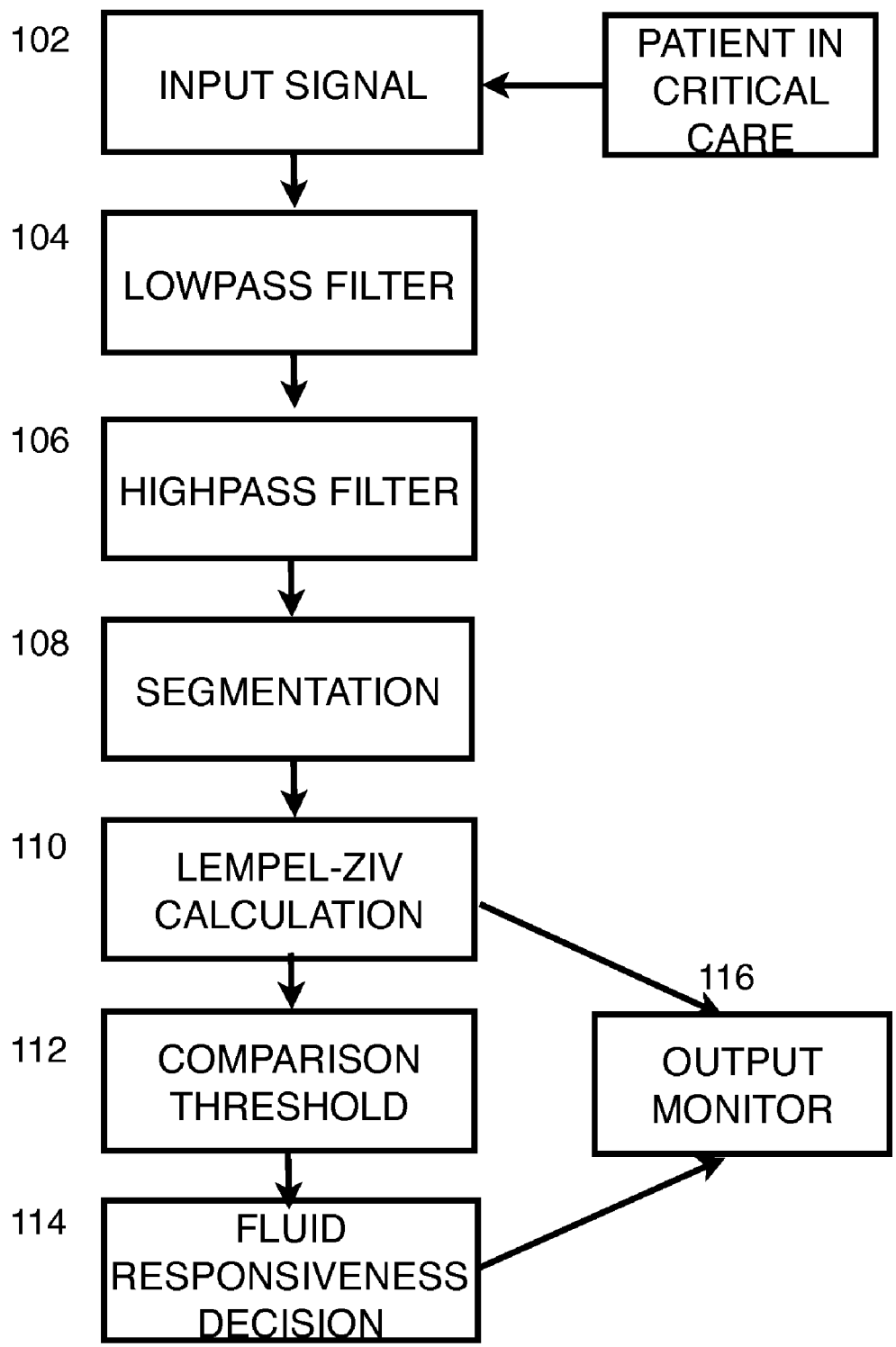
FIG. 1. Block diagram of the main components of the systems according to one embodiment of the invention.

FIG. 1 illustrates an embodiment of the method and apparatus for monitoring of fluid status and prediction of fluid responsiveness. The input physiologic signal (the arterial blood pressure or the photoplethysmographic signal) 102 is acquired from the patient in critical care, the signal is lowpass filtered 104, highpass filtered 106, segmented 108, the Lempel-Ziv metric is calculated for each segment 110, the result is compared against a threshold 112 to make the determination of fluid responsiveness 114. Both the output of the Lempel-Ziv calculation 110 and the binary decision regarding fluid responsiveness is displayed on the patient monitor 116. This method is implemented as part of a typical monitoring system used in intensive care units which includes sensors and acquisition modules to collect the necessary signals, hardware such as memory and processing units to record and process such biomedical signals according to the algorithm described herein, and an output display with user controls. The implementation of the fluid status monitoring method disclosed as part of such monitoring system is trivial for those of ordinary skill in the art.

Figure 2:
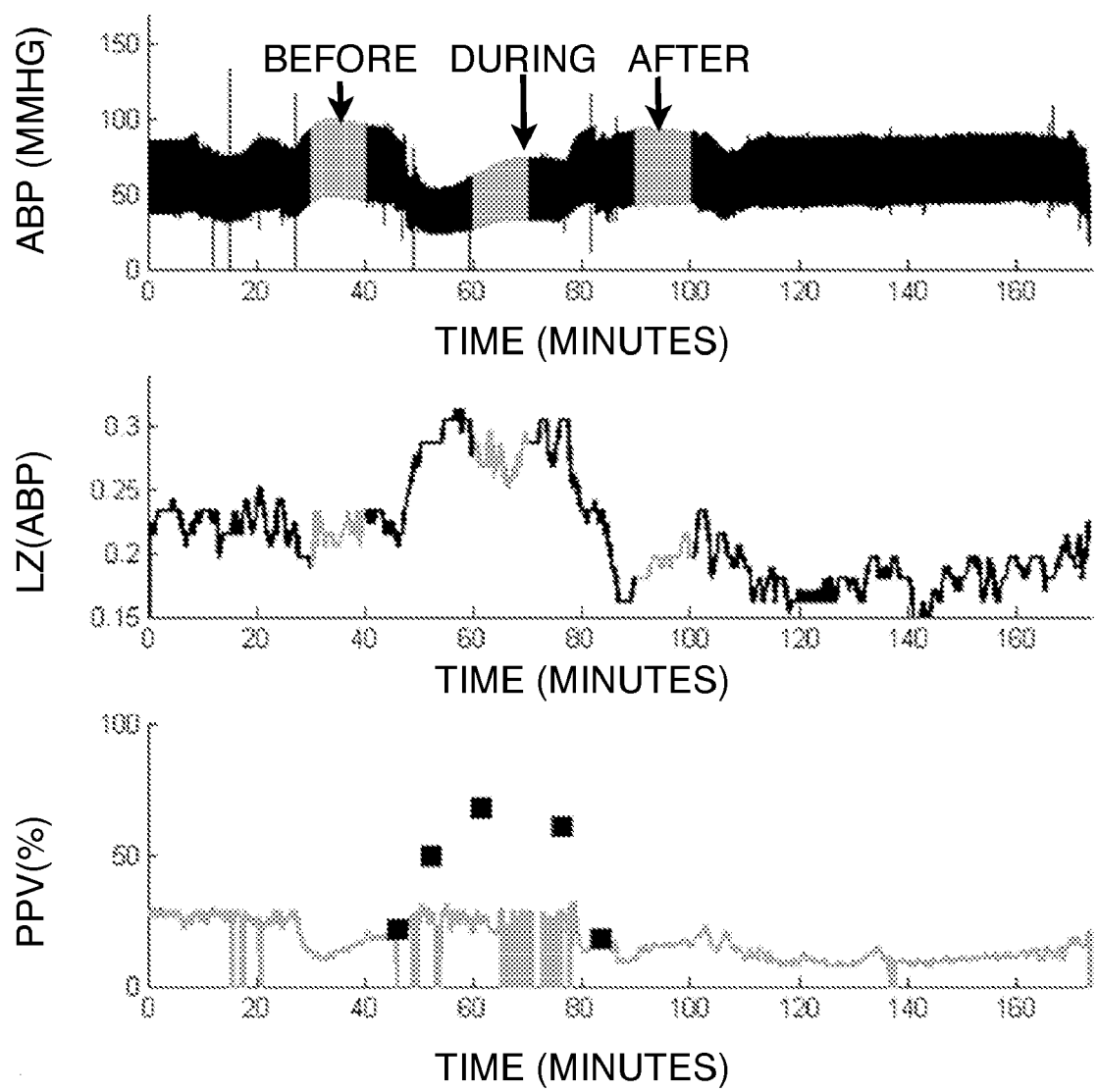
FIG. 2. Illustrative example of an input signal and the results obtained using one embodiment of the invention.

FIG. 2 shows a representative example of a real ABP signal during used during an experiment conducted to prove the usefulness of the proposed embodiment. LZ was evaluated on the ABP signal before injury ("before"), during hemorrhagic shock after injury ("during"), and after fluid resuscitation ("after"), using a moving window of 10 seconds. The bottom plot shows the estimated PPV using a commercial monitoring system. Five "gold standard? PPV manual annotations calculated by trained experts during periods of abrupt ABP changes are shown as black squares. FIG. 2 shows how LZ(ABP) correlates with the true values of fluid responsiveness. The advantage of LZ(ABP) is that is can be directly calculated from the input signal.

Below we describe how to calculate the LZ metric of any input signal x(n).

LZ complexity analysis is based on a coarse-graining of the measurements. Before calculating the LZ complexity measure c(n), the signal must be transformed into a finite symbol sequence. In the context of biomedical signal analysis, typically the discrete time biomedical signal x(n) is converted into a binary sequence. By comparison with the threshold $T_d$, the signal data are converted into a 0-1 sequence P as follows:

$$P=s(1), s(2), \ldots, s(n) \qquad (2)$$

where $$s(i) = \begin{cases} 0 & \text{if } x(i) < T_d \\ 1 & \text{otherwise} \end{cases} \qquad (3)$$

Usually the median is used as the threshold $T_d$ because of its robustness to outliers.

In order to compute LZ complexity, the sequence P is scanned from left to right and the complexity counter c(n) is increased by one unit every time a new subsequence of consecutive characters is encountered. The complexity measure can be estimated using the following algorithm:

1. Let S and Q denote two subsequences of P and SQ be the concatenation of S and Q, while sequence SQπ is derived from SQ after its last character is deleted (π denotes the operation of deleting the last character in the sequence). Let v(SQπ) denote the vocabulary of all different subsequences of SQπ. At the beginning, c(n)=1, S=s(1), Q=s(2), therefore, SQπ=s(1).
2. In general, S=s(1), s(2), . . . , s(r), Q=s(r+1), then SQπ=s(1), s(2), . . . , s(r); if Q belongs to v(SQπ), then Q is a subsequence of SQπ, not a new sequence.
3. Renew Q to be s(r+1), s(r+2) and judge if Q belongs to v(SQπ) or not.
4. Repeat the previous steps until Q does not belong to v(SQπ). Now Q=s(r+1), s(r+2), . . . , s(r+i) is not a subsequence of SQπ=s(1), s(2), . . . , s(r+i−1), so increase c(n) by one.
5. Thereafter, S is renewed to be S=s(1), s(2), . . . , s(r+i), and Q=s(r+i+1).

The above procedure is repeated until Q is the last character. At this time the number of different subsequences in P—the measure of complexity—is c(n). In order to obtain a complexity measure which is independent of the sequence length, c(n) must be normalized. If the length of the sequence is n and the number of different symbols in the symbol set is α, it has been proved that the upper bound of c(n) is given by:

$$c(n) < \frac{n}{(1-\epsilon_n)\log_\alpha(n)} \qquad (4)$$

where $\epsilon_n$ is a small quantity and $\epsilon_n \to 0 (n \to \infty)$. In general, $n/\log_\alpha(n)$ is the upper bound of c(n), where the base of the logarithm is α, i.e., $$\lim_{n \to \infty} c(n) = b(n) = \frac{n}{\log_\alpha(n)} \qquad (5)$$

For a 0-1 sequence, α=2, therefore $$b(n) = \frac{n}{\log_2(n)} \qquad (6)$$

and c(n) can be normalized via b(n):

$$C(n) = \frac{c(n)}{b(n)} \qquad (7)$$

C(n), the normalized LZ complexity, reflects the arising rate of new patterns in the sequence.

While particular embodiments of the present invention have been described, it is understood that modifications and generalizations will be apparent to those skilled in the art without departing from the spirit of the invention.

What is claimed is:

1. A method of monitoring fluid responsiveness comprising:
    (a) collecting a cardiac signal using a bedside monitoring apparatus comprising input sensors configured to collect and store cardiac signals,
    wherein said cardiac signal is an arterial blood pressure signal or a photoplethysmographic signal;
    (b) applying a lowpass filter and a highpass filter to remove local trend of said cardiac signal and eliminate unwanted noise;
    (c) calculating a Lempel-Ziv complexity metric of said cardiac signal after said applying lowpass filter and said highpass filter step; and
    (d) monitoring and displaying said Lempel-Ziv complexity metric to guide fluid therapy and assess fluid responsiveness by comparing said Lempel-Ziv complexity metric of said cardiac signal against a threshold higher than 0.23 to predict fluid responsiveness.

2. A method as in claim 1, further comprising segmenting said physiologic signal prior to said calculating Lempel-Ziv complexity step in order to obtain a plurality of Lempel-Ziv complexity metric results.

3. A method as in claim 1, where said cardiac signal is an arterial blood pressure signal.

4. A method as in claim 1, wherein said cardiac signal is a photoplethysmographic signal.

* * * * *